United States Patent [19]

Binder

[11] Patent Number: 4,587,428
[45] Date of Patent: May 6, 1986

[54] METHOD AND APPARATUS FOR THE DIAGNOSIS OF TISSUE SAMPLES

[76] Inventor: Arnold Binder, Im Münchfeld 9, 6500 Mainz 1, Fed. Rep. of Germany

[21] Appl. No.: 539,124

[22] Filed: Oct. 5, 1983

Related U.S. Application Data

[63] Continuation-in-part of Ser. No. 303,570, Sep. 18, 1981, abandoned.

[30] Foreign Application Priority Data

Sep. 29, 1980 [DE] Fed. Rep. of Germany ....... 3036610

[51] Int. Cl.$^4$ ................. G01N 21/59; G01N 21/51; G01N 9/24
[52] U.S. Cl. ................................. 250/372; 250/373; 250/252.1
[58] Field of Search ............... 128/665, 633; 250/373, 250/372, 252.1

[56] References Cited

U.S. PATENT DOCUMENTS

| | | | |
|---|---|---|---|
| 3,699,336 | 10/1972 | Ehrlich et al. | 250/461.2 |
| 3,854,050 | 12/1974 | Peterson et al. | 250/429 |
| 4,207,892 | 6/1980 | Binder | 128/665 |

FOREIGN PATENT DOCUMENTS

| | | | |
|---|---|---|---|
| 2709866 | 9/1977 | Fed. Rep. of Germany | 250/373 |
| 3036610 | 5/1982 | Fed. Rep. of Germany | 250/373 |

Primary Examiner—Alfred E. Smith
Assistant Examiner—Constantine Hannaher
Attorney, Agent, or Firm—Toren, McGeady, Stanger, Goldberg & Kiel

[57] ABSTRACT

A diagnostic technique to histologically detect malignancy and other tissue properties is performed by pressing a solid tissue sample between a pair of planar parallel plates transparent to ultraviolet light to a fraction of the original thickness of the sample and by subsequently passing focused ultraviolet light therethrough. The ultraviolet light is passed transversely to the planar glass plates and the emerging angularly distributed light is analyzed to determine a dignity parameter of the sample containing diagnostic information. In addition, a density parameter is obtained as a function of the portion of the ultraviolet light passing through the sample along the optical axis of the focused light. A diagnosis is obtained on the basis of the relationship between the dignity parameter and the density parameter.

10 Claims, 3 Drawing Figures

METHOD AND APPARATUS FOR THE DIAGNOSIS OF TISSUE SAMPLES

This application is a continuation-in-part of application Ser. No. 303,570, filed Sept. 18, 1981, abandoned.

The present invention relates generally to a method and apparatus for the diagnosis of tissue samples, and more particularly to a technique enabling relatively quick diagnosis of tumors.

More specifically, the invention is directed toward enabling histological tumor diagnosis by placement of a thick tissue sample which is compressed between a pair of small planar glass plates arranged parallel to each other, the sample being compressed to a fraction of its original thickness. The compressed sample is traversed with focused ultraviolet light which is directed along an optical axis extending generally perpendicularly to the glass plates and the ultraviolet radiation emerging in an angularly distributed pattern from the sample is analyzed for determining a dignity parameter containing diagnostic information. The dignity parameter thus obtained is a unique, monotonous and continuous function of the ratio of scatter coefficient to extinction coefficient of the compact tissue portion of the sample.

A method and apparatus of the type to which the present invention relates is disclosed and claimed in U.S. Pat. No. 4,207,892, and the present invention constitutes an improvement over this method and apparatus.

The method of U.S. Pat. No. 4,207,892 enables, with high diagnostic certainty, quick statements regarding the dignity of the tissue. That is, the prior art method enables a distinction to be determined between good or benign tissue and bad or malignant tissue. In malignant tumors, the prior art method and apparatus determines the degree of malignancy and diagnoses inflammatory changes in benign tissue. The prior art method permits, in particular, the examination of thick tissue samples without requiring prior preparation.

It has, however, been determined that the method in accordance with U.S. Pat. No. 4,207,892 involves the possibility of diagnostic error in certain special cases. For example, erroneous diagnoses could arise as a result of the dignity parameter when normal tissue is mixed in a sample with a substantial amount of fatty tissue. There then may result incorrect diagnoses of malignant tissue. Other causes for possible erroneous diagnoses can be lymphatic scissures in the stomach walls or partially edematous tissue.

The present invention is related to an improvement over the method and apparatus of U.S. Pat. No. 4,207,892, whereby elimination of such possible diagnostic errors in special cases may be achieved.

SUMMARY OF THE INVENTION

In accordance with the method of U.S. Pat. No. 4,207,892, histological diagnosis of tissue samples enabling quick diagnosis of tumors is accomplished by the steps of placing a solid tissue sample between a pair of planar members transparent to ultraviolet light, pressing the tissue sample between the members to a certain thickness substantially greater than the thickness of a single cell of the sample, passing focused ultraviolet light through the pressed sample in a direction transversely to the planar members, analyzing the angular distribution of ultraviolet radiation emerging from the sample, and determining a dignity parameter of the sample from the analysis of the angular distribution of the emerging ultraviolet radiation.

In accordance with the present invention, an improvement is provided in that in addition to determining the dignity parameter, there is also determined a density parameter based upon the portion of the ultraviolet light passing through the sample along the optical axis of the focused ultraviolet light. The density parameter, which supplies essential information concerning the optical density of the tissue sample, is used together with the dignity parameter in developing a diagnosis. Thus, the relationship, determined in dependence upon the type of tissue, between the dignity parameter and the density parameter is utilized as the basis for the diagnosis.

The ultraviolet light portion utilized in determining the density parameter is that portion of the ultraviolet light situated on the optical axis of the system. With the aid of the density parameter, and the dignity parameter determined in accordance with the method of U.S. Pat. No. 4,207,892, there may be established a data pattern which represents the determined interrelationships between these parameters and which enables, in accordance with the available findings, the achievement of diagnoses which approach in levels of accuracy thereof those of a normal routine histologist.

In the method in accordance with U.S. Pat. No. 4,207,892, tissue sample is traversed by ultraviolet light from a calibrated, stabilized ultraviolet source of radiation and the angular distribution of the ultraviolet radiation emerging from the tissue sample may be measured either goniometrically and scanned in such a manner as to form measurement signals by means of a movable ultraviolet detector or the angular distribution may be determined in such a manner that there are formed simultaneously incident measurement signals by means of several stationary ultraviolet detectors arranged angularly relative to the sample. With regard to the point of departure of the present invention, the method is performed in such a way that there is utilized as the density parameter the absolute value of the detector signal which appears at an angular setting of 0° relative to the optical axis.

If, however, a nonstabilized ultraviolet radiation source is used, then the method may be advantageously performed by establishing a relationship between an amplified detector signal derived at the angular setting of 0° and a reference signal derived from the ultraviolet light before it passes through the tissue sample, with the reference signal being amplified in such a way that the relationship of the signals corresponds to the density parameter determined at the same sample with a calibrated device. A device suitable for the performance of this alternative embodiment of the method of the invention may comprise elements arranged on the optical axis at defined distances from one another, said elements consisting of an ultraviolet light source, a monochromator, a collective lens which reproduces the exit aperture or slit of the monochromator on the sample, a pair of small glass plates which support the compressed sample, and an ultraviolet detector system arranged to receive ultraviolet radiation which emerges in an angularly distributed manner from the sample and which traverses fluorescent filters, with electronic processing devices connected after the ultraviolet detector arrangement for the detector signals. Such a device is characterized in that on the optical axis between the monochromator and the sample, preferably between the monochromator and the collective lens in the vicinity of the monochromator, there is arranged a partially translucent deflecting mirror by means of which a part of the ultraviolet light is deflected through a fluorescent filter arranged before a stationary reference detector, the reference signal of the detector being connected with the electronic processing devices which receive the other detector signals.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAILED DESCRIPTION OF THE PREFERRED EMBODIMENTS

Figure 1:
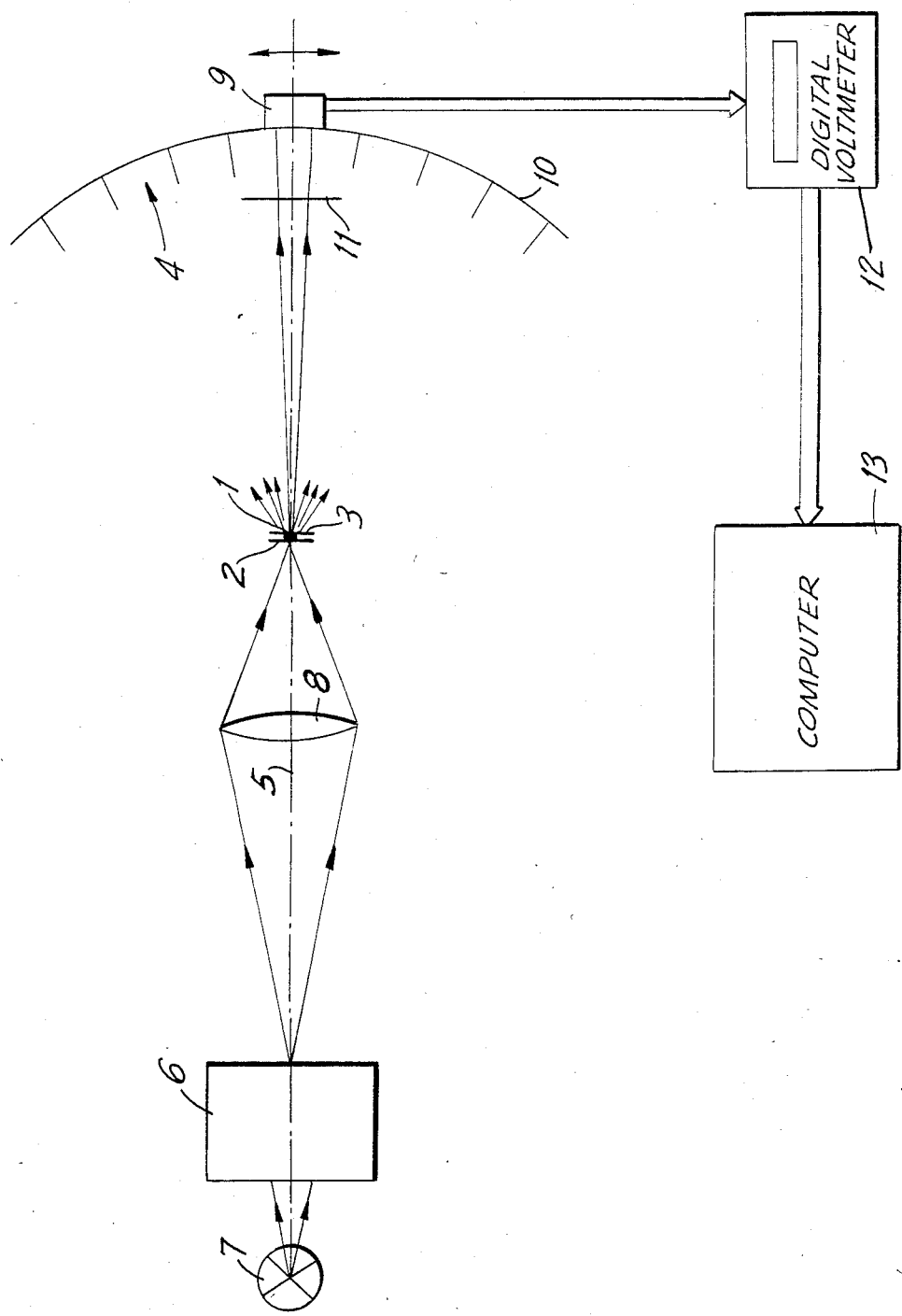
FIG. 1 is a schematic representation of an example of the basic apparatus to which the present invention relates which may also be utilized in the performance of the method in accordance with U.S. Pat. No. 4,207,892.
Figure 2:
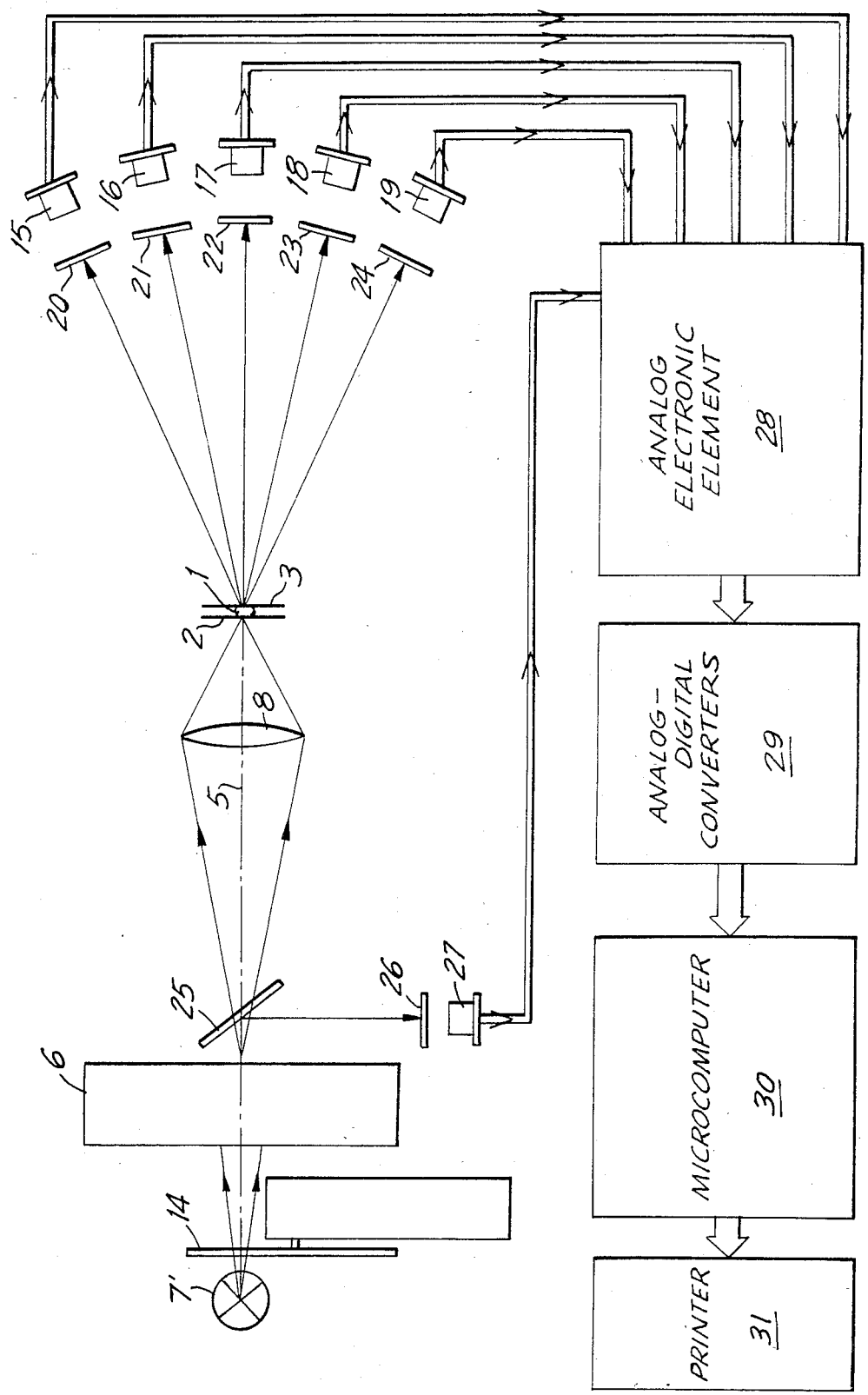
FIG. 2 shows a schematic illustration of a modified practical embodiment of the apparatus adapted for performing the method of the present invention.

Referring now to FIGS. 1 and 2, wherein similar parts are referred to by like reference numerals in each figure, a method in accordance with U.S. Pat. No. 4,207,892 may operate to enable establishment of a diagnostic parameter, the so-called dignity parameter, on the basis of a thick tissue sample 1 which may have a thickness of approximately 1 mm, by means of the device depicted in FIG. 1. The tissue sample 1 is exposed to ultraviolet light having a wave length of 366 nm.

The ultraviolet light is generated from an ultraviolet radiation source 7. The emitted radiation passes through a monochromator 6 and through a collective lens 8 whereby it is focused onto the tissue sample 1 which is pressed between a pair of object slides 2 and 3.

The angular distribution of the radiation emerging from the tissue sample is scanned by a detector 9 which is movably arranged on a graduated circle 10 of a goniometer 4.

A filter 11, which is translucent to the ultraviolet radiation having a wave length of 366 nm, prevents fluorescent light and visible light from passing to the detector. Analog signals of the detector 9 are converted into digital form in a digital voltmeter 12 and evaluated in a computer 13.

The system depicted in FIG. 1 comprises an optical axis 5 along which there are arranged the elements 7, 6, 8, 1, 2, 3, and 4.

A dignity parameter D is derived from the detector signals at different angular settings. The dignity parameter D is determined from the relationships of the individual detector signals. Specific value intervals of D are linked to specific diagnoses.

In the performance of the method in accordance with the present invention, apparatus similar to that depicted in FIG. 1 is utilized. However, in accordance with the present invention there is additionally determined a density parameter Z which is complementary to the dignity parameter D determined in accordance with the foregoing.

Since the ultraviolet radiation source 7 in the apparatus depicted in FIG. 1 is a calibrated, stabilized source of radiation, the parameter Z establishes itself as the absolute value of the calibrated detector 9 at an angular setting of 0° relative to the optical axis 5. The angular setting of 0° is characterized in that the axis of symmetry of the ultraviolet-sensitive surface of the detector 9 is on the optical axis 5 of the device. From the viewpoint of the radiation source 7, the detector 9 is behind the sample 1.

In a case where a non-stabilized ultraviolet radiation source is utilized, then there is used for the determination of the density parameter Z a method wherein this parameter is determined by means of two detectors. Apparatus suited for effecting this method is represented in FIG. 2 in an arrangement which is more suitable for actual practice than the more general arrangement depicted in FIG. 1.

In the arrangement depicted in FIG. 2, elements similar to those shown in FIG. 1 are identified by similar reference numerals. The ultraviolet light generated from the non-stabilized radiation source 7' passes through a light chopper 14 to the monochromator 6 and from there through the collective lens 8 to the tissue sample 1 which is compressed between the object slides 2 and 3. The ultraviolet radiation which emerges from the sample 1 will be in an angularly distributed pattern and will impinge onto a detector arrangement consisting of a plurality of ultraviolet detectors which are stationary and arranged symmetrically relative to the optical axis 5.

In the arrangement of FIG. 2, only five such detectors are depicted for the sake of simplicity, these detectors being the detectors 15, 16, 17, 18, and 19. Arranged in front of the detectors 15–19 are fluorescent filters 20, 21, 22, 23, and 24 which are arranged in operative relationship, respectively, with one of each of the detectors 15–19.

It will be noted that the detector 17 is situated at an angular setting of 0° relative to the optical axis 5.

Arranged on the optical axis 5 in the vicinity of the monochromator 6 is a stationary, partially translucent reflecting mirror 25 which permits part of the ultraviolet light emerging from the monochromator 6 to impinge upon a reference detector 27 through a fluorescent filter 26.

The detectors 15–19 and the detector 27 are connected with an analog electronic element 28 which comprises alternating current amplifiers, rectifiers, and analog averaging elements for the symmetrically arranged detectors 15–19.

The output of the analog electronic element 28 is applied to an arrangement 29 of analog-digital converters which are, in turn, connected to provide an input to a microcomputer 30 wherein calculation of the parameters D and Z and the establishment of a diagnosis occurs. Data from the microcomputer 30 are applied as an input to a printer 31 which operates to print out the parameters D and Z as well as the information representing a diagnosis.

With the apparatus in accordance with FIG. 2, the density parameter Z is determined in such a way that the ratio of the amplified signals is formed by the detector 17 and the reference detector 27. The amplification of the amplifiers inside the analog electronic element 28 is adjusted in such a manner that the ratio of the signals of the detectors 17 and 27 corresponds to a value of Z determined on the same sample on a calibrated device.

Based upon the data of the density parameter Z and the dignity parameter D, there may be established a data pattern furnishing the respective diagnosis corresponding to the respective association between D and Z. Such a data pattern for lymph node metastases in stomach cancer (carcinoma) is represented by way of example in the following Table I:

TABLE I

| $D \cdot 10^5$ | Z | Diagnosis |
|---|---|---|
| $\leq 850$ | optional | benign |
| $850 < D \leq 1200$ | $\leq 10\,000$ | benign |
| $850 < D \leq 1200$ | $10\,000 < Z \leq 11\,500$ | metastasis |
| $850 < D \leq 1200$ | $>11\,500$ | benign |
| $1200 < D \leq 1310$ | $\leq 16\,000$ | benign |
| $1200 < D \leq 1310$ | $16\,000 < Z \leq 18\,000$ | metastasis |
| $>1310$ | optional | benign |
| optional | $>18\,000$ | benign |

The absolute value of the density parameter Z in a specific example is thus determined by convention. To this determination there is then assigned a histological statement. The dignity parameter D is determined through the analog electronic equipment 28 which, for each of the detectors 15–19, supplies the same output signal when the detectors are submitted to the same radiation intensity at a wave length of 366 nm. The analog electronic element and the detectors must thereat operate in the linear area or range.

When practicing the method in the laboratory, it has been found that a sample size (uncompressed) having maximum dimensions of $3 \times 6$ mm is particularly effective. To avoid disturbed measurement signals at the detectors, provision should be made to ensure that in the vicinity of the sample, that is to say in a radius of approximately 40 mm, there will not be located any components which might significantly influence the ultraviolet radiation.

The dignity parameter is a function of the intensity I of the radiation sensed at the ultraviolet detectors. Generally, the relationship between the dignity parameter and the sensed levels of intensity $I_{15}$–$I_{19}$ for each of the detectors 15–19, respectively, may be stated as $D = f$ $I_{15}/I_{17}$; $I_{16}/I_{17}$; $I_{18}/I_{17}$; $I_{19}/I_{17}$.

The density parameter Z is represented as a function of the absolute $I^{17}$.

Figure 3:
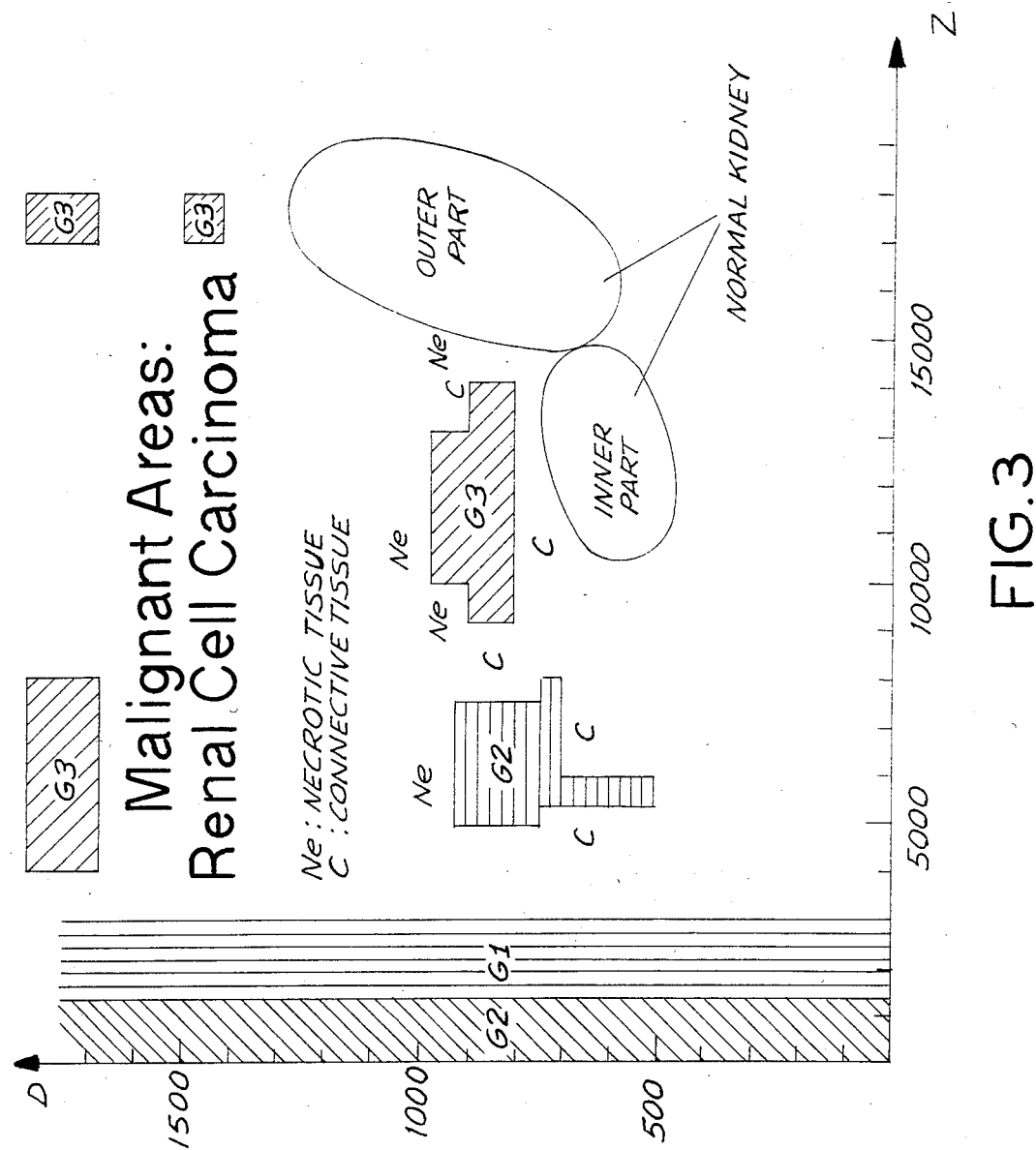
FIG. 3 is a graph or D/Z diagram plotting dignity parameter against density parameter correlated with kidney tissue, more specifically with renal parenchyma.

Before determining the diagnoses of specific tissue samples, there is first constructed a D/Z diagram for the specific type (organ) of the tissue samples to be scanned. An example of such a diagram is shown in FIG. 3. The diagram of FIG. 3 is a D/Z diagram correlated with kidney tissue, more specifically with renal parenchyma. As will be apparent from FIG. 3, values of D are plotted against values of Z. D/Z diagrams of other organs are not identical with the kidney diagram shown in FIG. 3.

All diagrams for the different types of tissue which are to be diagnosed are constructed by comparison with results of conventional histology.

With reference to FIG. 3, the hatched areas of the D/Z diagram for kidney samples are correlated with malignancy. This means that if one or more couples of the dignity parameters and the density parameters determined from a renal tissue sample fix points which are situated within the hatched areas, the sample contains a malignant tumor.

It will be understood that the manner in which the tissue sample is scanned may vary and the dimensions of the scanning pattern will depend upon the required accuracy. For example, minimum accuracy of scanning would correlate with a single pattern point per sample. Of course, higher standards of accuracy would be correlated with higher numbers of scans and minimal distances between pattern points. This is comparable with conventional paraffin histology. For normal routine histological examination, only 1 to 3 sections of a 1 mm thick tissue sample are prepared. For higher accuracy, the number of sections is higher and may be 100 sections or more.

The procedure of performing a diagnosis is as follows: for each point of the scanning pattern of the tissue sample, a couple of the dignity parameter and the density parameter is determined as previously described herein. The couples or readings of dignity parameters and density parameters are compared with the D/Z diagram, for example a diagram such as that shown in FIG. 3, and if the comparison indicates malignancy for one or more couples of the values D and Z, then the tissue can be considered to contain malignant parts. Other tissue characteristics can be determined in the same manner.

In addition to diagnosis of malignancy, the grade of the malignancy or the so-called histological grade can also be stated by the D/Z diagram as well as other tissue characteristics. A closer examination of the D/Z diagram shown by way of example in FIG. 3 will show that the malignant areas contain designations G1, G2, G3. For example, the areas denoted G3 are correlated with malignant tissue of histological grade G3. For the designations G1 and G2, the same correlation applies regarding histological grades G1 and G2.

The histological grade of a tumor is determined by the highest grade of all the tissue samples of the tumor. Grade G1 is correlated with excellent survival rates, and grade G3 would indicate poor survival possibilities. The histological grade is also important for the therapy applied for the tumor.

While specific embodiments of the invention have been shown and described in detail to illustrate the application of the inventive principles, it will be understood that the invention may be embodied otherwise without departing from such principles.

What is claimed is:

1. In a method for histological diagnosis of tissue samples, particularly for effecting quick diagnosis of tumors, including the steps of placing a solid tissue sample between a pair of planar members transparent to ultraviolet light, pressing said sample between said members to a certain thickness substantially greater than the thickness of a single cell of said sample, passing focused ultraviolet light having an optical axis through the pressed sample in a direction transversely to said planar members, analyzing the angular distribution of ultraviolet radiation emerging from said sample and determining a dignity parameter of said sample from said analysis of said angular distribution of said emerging ultraviolet radiation, the improvement comprising determining a density parameter which is representative of information relating to the optical density of said tissue sample by sensing the portion of said ultraviolet light passing centrally through said tissue sample along the optical axis of said focused ultraviolet light, said density parameter being thus determined on the basis of said portion of said ultraviolet light passing through said tissue sample along said optical axis of said focused ultraviolet light and obtaining a diagnosis of said tissue sample on the basis of the relationship between said dignity parameter and said density parameter.

2. A method according to claim 1 wherein said ultraviolet light passed through said tissue sample is provided from a calibrated stabilized radiation source and wherein said angular distribution of ultraviolet radiation emerging from said tissue sample is measured by being scanned goniometrically with a movable ultraviolet detector to generate measurement signals.

3. A method according to claim 1 wherein said ultraviolet light passed through said tissue sample is provided from a calibrated stabilized radiation source and wherein said angular distribution of ultraviolet radiation emerging from said tissue sample is measured by means of a plurality of stationary ultraviolet detectors angularly arranged relative to the optical axis of said focused ultraviolet light and operating to simultaneously develop incident measurement signals.

4. A method according to claim 2 wherein said density parameter is determined as a function of the absolute value of ultraviolet radiation coincident with the optical axis of said focused ultraviolet light.

5. A method according to claim 3 wherein said density parameter is determined as a function of the absolute value of ultraviolet radiation coincident with the optical axis of said focused ultraviolet light.

6. A method according to claim 2 wherein said relationship between said dignity parameter and said density parameter is determined on the basis of an amplified detector signal derived from ultraviolet radiation coincident with said optical axis of said focused ultraviolet light and a reference signal derived from ultraviolet light sensed before being passed through said sample, said reference signal being amplified in such a manner that the relationship of the signals corresponds to the density parameter determined at the same sample with a calibrated device.

7. A method according to claim 3 wherein said relationship between said dignity parameter and said density parameter is determined on the basis of an amplified detector signal derived from ultraviolet radiation coincident with said optical axis of said focused ultraviolet light and a reference signal derived from ultraviolet light sensed before being passed through said sample, said reference signal being amplified in such a manner that the relationship of the signals corresponds to the density parameter determined at the same sample with a calibrated device.

8. A method according to claim 1 wherein a reference signal is derived from said ultraviolet light before it is passed through said sample, said reference signal being used to compare said ultraviolet light with ultraviolet light from a calibrated source to compensate for deviations in the source of said ultraviolet light.

9. A method according to claim 8 wherein said reference signal is derived from ultraviolet light reflected from a partially translucent mirror located between a source of said ultraviolet light and said tissue sample.

10. Apparatus for the histological diagnosis of tissue samples, utilizing solid tissue samples particularly for effecting a quick diagnosis of tumors, comprising:
a pair of planar plates transparent to ultraviolet light for pressing therebetween a solid tissue sample to be diagnosed;
a source of ultraviolet light arranged to direct said light through said tissue sample pressed between said planar plates;
lens means located between said tissue sample and said light source;
monochromator means having an exit slit projected onto said sample by said lens means;
ultraviolet detector means arranged to receive ultraviolet light passing through said tissue sample in an angularly distributed manner;
electronic information processing means arranged to receive signals from said detector means;
partially translucent mirror means located along the optical axis of said lens means operative to reflect part of the ultraviolet light emanating from said light source; and
reference detector means arranged to sense said reflected ultraviolet light to produce a reference signal in response thereto and to apply said signal into said electronic information processing means together with said signals from said detector means.

* * * * *